United States Patent [19]

Nuebling et al.

[11] Patent Number: 5,593,943
[45] Date of Patent: Jan. 14, 1997

[54] HETEROAROMATICALLY CONDENSED HYDROXYPYRIDONECARBOXAMIDES, THEIR PREPARATION AND USE AS HERBICIDES

[75] Inventors: Christoph Nuebling, Hassloch; Wolfgang von Deyn, Neustadt; Hans Theobald, Limburgerhof; Karl-Otto Westphalen, Speyer; Uwe Kardorff, Mannheim; Helmut Walter, Obrigheim, all of Germany; Thomas Kappe, Graz, Austria; Matthias Gerber, Limburgerhof, Germany

[73] Assignee: BASF Aktiengesellschaft, Ludwigshafen, Germany

[21] Appl. No.: 261,967

[22] Filed: Jun. 17, 1994

Related U.S. Application Data

[62] Division of Ser. No. 107,303, Aug. 17, 1993, Pat. No. 5,378,679.

[30] Foreign Application Priority Data

Aug. 21, 1992 [DE] Germany ............ 42 27 747.7

[51] Int. Cl.⁶ .......... C07D 401/06; C07D 401/02; A01N 43/42; A01N 43/44
[52] U.S. Cl. .......... 504/221; 504/226; 504/246; 504/247; 546/113; 546/114; 546/116; 546/117; 546/118; 546/119; 546/120; 544/61; 544/127; 544/362
[58] Field of Search .............. 546/183, 113, 546/114, 116, 117, 118, 119, 120; 514/300, 301, 302, 303; 504/246, 221, 226, 247, 246; 544/61, 127, 362

[56] References Cited

U.S. PATENT DOCUMENTS

| | | | |
|---|---|---|---|
| 4,215,123 | 7/1980 | Scotese et al. | 424/256 |
| 4,215,216 | 7/1980 | Scotese et al. | 544/117 |
| 4,877,793 | 10/1989 | Davies | 514/301 |
| 5,112,832 | 5/1992 | Crossley et al. | 514/299 |
| 5,155,115 | 10/1992 | Suzuki et al. | 514/301 |
| 5,219,864 | 6/1993 | Suzuki et al. | 514/301 |
| 5,352,685 | 10/1994 | Maruyama et al. | 514/301 |
| 5,378,679 | 1/1995 | Nuebling et al. | 504/246 |

FOREIGN PATENT DOCUMENTS 826926 6/1975 Belgium.

OTHER PUBLICATIONS

J. Chem Soc., Perkin Trans. I, 1990, 2943.
J. Chem. Soc., Perkin Trans. I, 1982, 2391.
J. Heterocycl. Chem. 14(1977) 435–38.
J. Heterocycl. Chem. 15, (1978) 319–20.
J. Chem. Res. (S) 1980, 6–7.
J. Chem. Res. (S) 1989, 196–7.
J. Chem Soc. 1963, 491.
J. Med Chem. 30 (1987) 2270–77.
JP-A 59210–093 (CA 102) 166772 c) 1984.
Pol. J. Chem. 52 (1978) 1269–76.
Roczniki ChemII, Ann. Soc. Chim. Polonorum 48, 1815–20 (1974).

*Primary Examiner*—Matthew V. Grumbling
*Attorney, Agent, or Firm*—Keil & Weinkauf

[57] ABSTRACT

Heteroaromatically condensed hydroxypyridonecarboxamides of the structure I

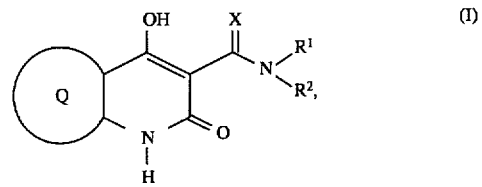

where the substituents and the ring Q have the following meanings:

$R^1$ hydrogen, hydroxyl, substituted or unsubstituted alkyl, alkenyl, alkynyl, cycloalkyl, alkoxy;

$R^2$ hydrogen, substituted or unsubstituted alkyl, alkenyl, alkynyl, cycloalkyl, alkenyloxy, dialkylamino;

or $R^1$, $R^2$ together denote an alkylene chain with 2–6 members and which may be interrupted by oxygen, sulfur or N-methyl;

X oxygen or sulfur;

Q a 5- or 6-membered heteroaromatic ring containing from 1 to 3 nitrogen atoms and/or one oxygen or sulfur atom as heteroatoms, and which may be substituted one to three times, and environmentally compatible salts thereof.

5 Claims, No Drawings

HETEROAROMATICALLY CONDENSED HYDROXYPYRIDONECARBOXAMIDES, THEIR PREPARATION AND USE AS HERBICIDES

This is a division of Ser. No. 08/107,303 filed Aug. 17, 1993, now U.S. Pat. No. 5,378,679.

The present invention relates to heteroaromatically condensed hydroxypyridonecarboxamides of the structure I

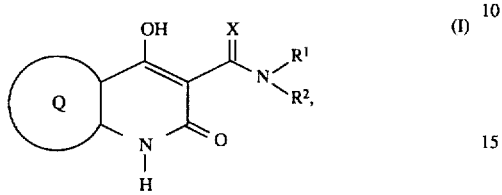

where the substituents and the ring Q have the following meanings:

- $R^1$ is hydrogen, hydroxyl, $C_1$–$C_{12}$-alkyl, $C_3$–$C_{12}$-alkenyl, $C_3$–$C_{12}$-alkynyl, $C_3$–$C_8$-cycloalkyl or $C_1$–$C_{12}$-alkoxy, where the organic radicals are substituted or unsubstituted;
- $R^2$ is hydrogen, $C_1$–$C_{12}$-alkyl, $C_3$–$C_{12}$-alkenyl, $C_3$–$C_{12}$-alkynyl, $C_3$–$C_8$-cycloalkyl, $C_3$–$C_8$-alkenyloxy or di-$C_1$–$C_4$-alkylamino, where the organic radicals are substituted or unsubstituted;

or

- $R^1$, $R^2$ together denote an alkylene chain having 2–6 members which may be interrupted by oxygen, sulfur or N-methyl;
- X is oxygen or sulfur;
- Q is a 5- or 6-membered heteroaromatic ring containing 1 to 3 nitrogen atoms and/or one oxygen or sulfur atom as heteroatoms, and which is unsubstituted or mono- to trisubstituted, and environmentally compatible salts thereof.

In particular, the invention relates to heteroaromatically condensed hydroxypyridonecarboxamides of the general formula I

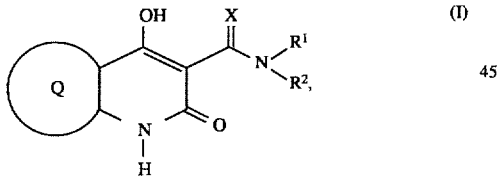

where the substituents and the ring Q have the following meanings:

- $R^1$ hydrogen, hydroxyl, $C_1$–$C_{12}$-alkyl, $C_3$–$C_{12}$-alkenyl, $C_3$–$C_{12}$-alkynyl, $C_3$–$C_8$-cycloalkyl or $C_1$–$C_{12}$-alkoxy, where these groups may carry the following radicals:

halogen, cyano, $C_3$–$C_8$-cycloalkyl, $C_1$–$C_4$-alkoxy, $C_1$–$C_4$-alkylthio, $C_1$–$C_4$-haloalkylthio, $C_1$–$C_4$-haloalkoxy, di-$C_1$–$C_4$-alkylamino, phenyl, phenoxy or phenylthio, where the phenyl radicals in turn may carry from one to three of the following groups: halogen, $C_1$–$C_4$-alkyl, cyano, nitro, $C_1$–$C_4$-alkoxy, $C_1$–$C_4$-haloalkyl or $C_1$–$C_4$-haloalkoxy

- $R^2$ hydrogen, $C_1$–$C_{12}$-alkyl, $C_3$–$C_{12}$-alkenyl, $C_3$–$C_{12}$-alkynyl, $C_3$–$C_8$-cycloalkyl, $C_3$–$C_8$-alkenyloxy or di-$C_1$–$C_4$-alkylamino, where these groups may carry the following radicals: halogen, cyano, $C_3$–$C_8$-cycloalkyl, $C_1$–$C_4$-alkoxy, $C_1$–$C_4$-alkylthio, $C_1$–$C_4$-haloalkoxy, $C_1$–$C_4$-haloalkylthio, phenyl, phenoxy, phenylthio, where the phenyl radicals in turn may carry from one to three of the following groups: halogen, $C_1$–$C_4$-alkyl, $C_1$–$C_4$-alkoxy, cyano or nitro;

or

- $R^1$, $R^2$ together denote an alkylene chain with 2–6 members and which may be interrupted by oxygen, sulfur or N-methyl;
- X oxygen or sulfur
- Q a 5- or 6-membered heteroaromatic ring containing 1–3 nitrogen atoms and/or an oxygen or a sulfur atom as heteroatoms, and which may bear from one to three of the following radicals: halogen, nitro, cyano, $C_1$–$C_4$-alkyl, $C_1$–$C_4$-alkoxy, $C_1$–$C_4$-alkylthio, $C_1$–$C_4$-alkoxy-$C_1$–$C_4$-alkyl, $C_3$–$C_8$-cycloalkyl, $C_2$–$C_4$-alkenyl, phenyl or phenyl-$C_1$–$C_4$-alkyl, where the phenyl radicals in turn may carry from one to three of the following groups: halogen, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy;

and their environmentally tolerated salts.

The invention furthermore relates to the manufacture of compounds I and their use as herbicides.

It is known that 1-phenyl-substituted 4-hydroxy-1,8-naphthyrid-2-one-3-carboxamides have inflammation-inhibiting properties (J. Med. Chem. 35 (1992) 1130 and EP-A 452873). However, there is no indication in the art of a herbicidal action. German Applications P 41 38 819.4 and P 41 38 820.8 disclose non-condensed hydroxylpyridonecarboxamides and hydroxyquinolinecarboxamides.

The object of the invention was to provide novel hydroxypyridonecarboxamides having a good herbicidal action, and processes for manufacturing them.

We have found the heteroaromatically condensed hydroxypyridonecarboxamides of the formula I defined at the outset, processes for their manufacture, and herbicidal agents containing compounds I.

The compounds of the formula I may be present in the following tautomeric forms, which are also encompassed by the invention:

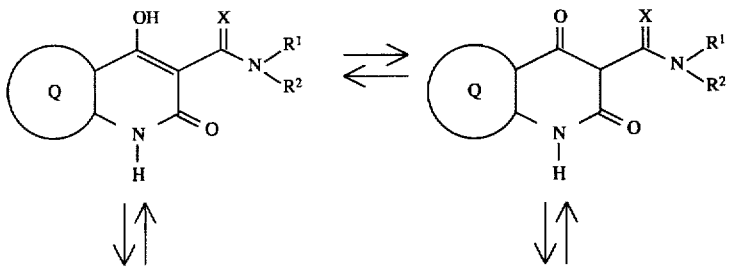

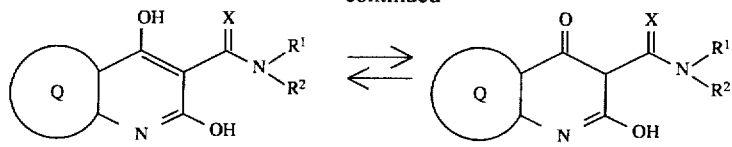

The compounds I are manufactured by reacting compounds of the formula II

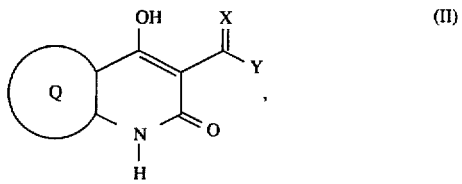

where X and Q have the above meanings and Y is hydroxyl, halogen or a conventional nucleofugic leaving group, with an amine of the formula III

where $R^1$ and $R^2$ have the meanings given above.

The reaction is usually carried out at from 20° C. to 250° C., preferably 100° C. to 180° C., in an inert organic solvent.

Examples of suitable solvents or diluents are aliphatic, alicyclic and aromatic hydrocarbons, such as pentane, hexane, cyclohexane, benzene, toluene, xylenes; ethers such as diethyl and di-n-butyl ether, methyl tert-butyl ether, dimethoxyethane, ethylene glycol dimethyl ether, tetrahydrofuran and dioxane; alcohols such as methanol, ethanol, propanol and butanol, aprotic dipolar solvents such as dimethylformamide, dimethylsulfoxide and pyridine.

It is also possible to employ mixtures of these substances as solvents and diluents.

The starting materials are usually employed in stoichiometric amounts. It may be advantageous, for example to increase the yield, to use one of the starting materials, preferably the amine, in an excess of from 0.1 to 10 mole equivalents.

The reaction is generally carried out at atmospheric pressure. It may, however, be advantageous, depending on the type of amine or solvent employed, to carry out the reaction at increased pressure, especially at autogenously increased pressure, in an autoclave.

For the amidation reaction, the type of nucleofugic leaving group Y used in the hydroxypyridonecarboxamide derivative II plays no important role, which means that it is preferable to use derivatives II which are readily and inexpensively accessible. Y may denote, in addition to OH and halogen (especially chorine and bromine), a group OR or SR, R denoting an aliphatic, cycloaliphatic or araliphatic radical. It is advantageous to react the free carboxylic acids (Y=OH), the acid halides, especially acid chlorides (Y=Cl) or the esters or thioesters, with low molecular weight alkyl radicals (Y=OR, SR where R=$C_1$–$C_6$-alkyl, e.g., methyl or ethyl).

The compounds of the formula I are also obtained in one stage from the corresponding acids II (X=O, Y=OH) by reaction with an amine III in the presence of a dehydrating agent such as dicyclohexylcarbodiimide at temperatures of from 0°–100° C., preferably from 0°–30° C. in an inert solvent such as dichloromethane, tetrahydrofuran, toluene or ethyl acetate. Such reactions are described for instance in WO 90/15052.

The acids II (X=O, Y=OH) can be obtained from the esters II (X=O, Y=O-alkyl) by hydrolysis with barium hydroxide in conventional manner (J. Chem. Soc. 1963, 491).

The amines III required for the reactions are either known, commercially available, or can be obtained by generally known chemical processes.

The starting materials of the formula II are either known or can be prepared by generally known processes. Naphthyridinecarboxylates of the formula II (Q=pyridine) are disclosed for example in: J. Med. Chem. 30 (1987) 2270; J. Prakt. Chem. 333 (1991) 637; U.S. Pat. No. 4,215,123; Pol. J. Chem. 52(1978) 2369 and Rocz. Chem. 48 (1974) 1815 (CA 82, 111959 g). Pyridopyrimidines of the formula II (Q=pyrimidine) are disclosed for example in: Chem. Ber. 96 (1963) 1868 and JP-A 59210-093 (CA 102, 166772 c), N-alkylated derivatives e.g. in U.S. Pat. No. 4,215,216. Thienopyridines of the formula II (Q=thiophene) are described for example in: J. Chem. Res. (S) 1989, 196; J. Chem. Res. (S) 1985, 214 and J. Chem. Res. (S) 1980, 6. Pyrazolopyridines of the formula II (Q=pyrazole) are described for example in: J. Heterocycl. Chem. 15 (1978) 319 and J. Chem. Soc., Perkin Trans. I, 1990, 2943. Isoxazolopyridines of the formula II (Q=isoxazole) are described for example in: J. Chem. Soc., Perkin Trans. I, 1982, 2391 and J. Heterocycl. Chem. 14(1977) 435. Pyrrolopyridines of the formula II (Q=pyrrole) may be prepared analogously to the method disclosed in BE- A 826 926. The starting materials of the formula II not expressly mentioned here may be prepared analogously to the cited methods by condensation of a heterocyclic 1-amino-2-carboxylate with a malonic acid derivative.

In view of the intended use of the heteroaromatically condensed hydroxypyridonecarboxamides of the formula I, the radicals given below are suitable substituents:

$R^1$ hydrogen,
  branched or straight-chain $C_1$–$C_{12}$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl, 1-ethyl-2-methylpropyl, heptyl, 1-methylheptyl, octyl, nonyl, decyl, undecyl and dodecyl,
  especially $C_1$–$C_6$-alkyl such as methyl, ethyl, 1-methylethyl, 1-methylpropyl, 2-methylpropyl, 1,1-dimethylethyl and 1,1-dimethylpropyl;
  branched or straight-chain $C_3$–$C_{12}$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, ethyl-2-methyl-2-propenyl and 10-undecenyl, especially $C_3$–$C_6$-alkenyl such as 2-propenyl, 2-butenyl, 3-butenyl, 1-methyl-2-propenyl, 2-methyl-2-propenyl 1-methyl-2-butenyl and 1,1-dimethyl-2-propenyl;

$C_3$–$C_{12}$-alkynyl, especially $C_3$–$C_6$-alkynyl such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_3$–$C_8$-cycloalkyl such as cyclopropyl, cyclobutyl, cyclopentyl, cyclohexyl, cycloheptyl, cyclooctyl, especially cyclopropyl and cyclohexyl; $C_1$–$C_{12}$-alkoxy, especially $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 1,1-dimethylpropyloxy, 1,2-dimethylpropyloxy, 2,2-dimethylpropyloxy, 1-ethylpropyloxy, hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy, where the abovementioned organic groups may bear from one to five halogen atoms such as fluorine, chlorine, bromine or iodine, preferably fluorine, chlorine and bromine, and/or from one to three of the following radicals:

cyano;

$C_3$–$C_8$-cycloalkyl, such as cyclopropyl, cyclobutyl, cyclopentyl, cyclohexyl, cycloheptyl, cyclooctyl, especially cyclopropyl and cyclohexyl;

$C_1$–$C_4$-alkoxy such as methoxy, ethoxy, n-propoxy, 2-methylethoxy, n-butoxy, 1-methylpropoxy, 2-methylpropoxy and 1,1-dimethylethoxy, especially methoxy and ethoxy;

$C_1$–$C_4$-haloalkoxy such as chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy, 2,2,2-trifluoroethyloxy and 2-chloro-2,2-difluoroethoxy;

$C_1$–$C_4$-alkylthio such as methylthio, ethylthio, n-propylthio, 1-methylethylthio, n-butylthio, 1-methylpropylthio, 2-methylpropylthio and 1,1-dimethylethylthio, especially methylthio;

$C_1$–$C_4$-haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dicloro-2-fluoroethylthio, 2,2,2-trichloroethylthio and pentafluoroethylthio, especially trichloromethylthio;

di-$C_1$–$C_4$-alkylamino such as dimethylamino, diethylamino, dipropylamino, dibutylamino, N-methyl-N-ethylamino, N-methyl-N-propylamino, N-methyl-N-1-methylethylamino, N-methyl-N-1,1-dimethylethylamino, di-1-methylethylamino, N-ethyl-N-1-methylethylamino and N-ethyl-N-1,1-dimethylethylamino;

phenyl, phenylthio, phenoxy, where the phenyl radicals in turn may carry from one to five halogen atoms such as fluorine, chlorine, bromine and iodine, especially fluorine and chlorine, and/or one to three of the following groups:

cyano or nitro;

$C_1$–$C_4$-alkyl, as mentioned above, especially methyl, ethyl, propyl, 1-methylpropyl and 1,1-dimethylpropyl;

$C_1$–$C_4$-haloalkyl, especially trifluoromethyl;

$C_1$–$C_4$-alkoxy, as mentioned above, especially methoxy and ethoxy;

$C_1$–$C_4$-haloalkoxy, as mentioned above, especially trifluoromethoxy;

$R^2$ hydrogen, $C_1$–$C_{12}$-alkyl, $C_3$–$C_{12}$-alkenyl, $C_3$–$C_{12}$-alkynyl, $C_3$–$C_8$-cycloalkyl, each as mentioned above generally and specifically for $R^1$ $C_3$–$C_8$-alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 3-methyl-2-butenyloxy, 1-methyl-2-butenyloxy, 2-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-4-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and ethyl-2-methyl-2-propenyloxy, especially 2-propenyloxy;

di-$C_1$–$C_4$-alkylamino, as mentioned above for $R^1$, where the above organic groups may carry from one to five halogen atoms such as fluorine, chlorine, bromine or iodine, preferably fluorine, chlorine and bromine, and/or one to three of the following radicals:

cyano, $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio and di-$C_1$-$C_4$-alkylamino, each as mentioned individually above, phenyl, phenylthio, phenoxy, where the phenyl radicals in turn may carry from one to five halogen atoms such as fluorine, chlorine, bromine and iodine, especially fluorine and chlorine, and/or one to three of the following groups:

cyano or nitro, $C_1$-$C_4$-alkyl, $C_1$-$C_4$-alkoxy, each as mentioned above;

$R^1$ and $R^2$ together denote a $C_2$-$C_6$-alkylene chain which may be interrupted by oxygen, sulfur or N-methyl, such as $(CH_2)_2$, $—(CH_2)_3—$, $—(CH_2)_4—$, $—(CH_2)_5—$, $—(CH_2)_6—$, $—CH_2—O—CH_2—$, $—CH_2—CH_2—O—CH_2—CH_2—$, $—CH_2—S—CH_2—$, $—CH_2—CH_2—S—CH_2—CH_2—$, $—CH_2—N(CH_3)—CH_2—CH_2—$, especially $—(CH_2)_5—$ and $—CH_2—CH_2—O—CH_2—CH_2—$;

X oxygen or sulfur;

Q a 5- or 6-membered heteroaromatic ring containing 1–3 nitrogen atoms and/or one oxygen or sulfur atom as heteroatoms, such as pyridine, pyrimidine, pyrazine, pyridazine, triazine, thiophene, furan, pyrrole, oxazole, isoxazole, thiazole, isothioazole, pyrazole, imidazole, triazole, oxadiazole and thiadiazole, which is linked to the hydroxypyridone ring via adjacent carbon atoms and may carry from one to three of the following radicals:

halogen such as fluorine, chlorine, bromine and iodine, especially fluorine and chlorine, cyano and/or nitro, $C_1$-$C_4$-alkyl, as mentioned above, especially methyl, ethyl, propyl, 1-methylethyl and 1,1-dimethylethyl, $C_1$-$C_4$-alkoxy, as mentioned above, especially methoxy and ethoxy, $C_1$-$C_4$-alkylthio, as mentioned above, especially methylthio and ethylthio, $C_1$-$C_4$-alkoxyalkyl, especially methoxymethyl, ethoxymethyl and methoxyethyl, $C_3$-$C_8$-cycloalkyl as mentioned above, especially cyclopropyl and cyclohexyl, $C_2$-$C_4$-alkenyl, especially ethenyl and propenyl, phenyl, phenyl-$C_1$-$C_4$-alkyl, especially benzyl and phenylethyl, where the phenyl groups in turn may carry from one to three of the following groups: halogen, $C_1$-$C_4$-alkyl, $C_1$-$C_4$-alkoxy, $C_1$-$C_4$-alkylthio, each as mentioned above, $C_1$-$C_4$-haloalkyl, especially trifluoromethyl $C_1$-$C_4$-haloalkoxy, especially trifluoromethoxy.

Suitable salts of compounds I are agriculturally utilizable salts, for example alkali metal salts, especially potassium and sodium, alkaline earth metal salts, especially calcium, magnesium and barium, manganese, copper, zinc or iron salts, and ammonium, phosphonium, tetraalkylammonium salts, benzyltrialkylammonium salts, trialkylsulfonium salts or trialkylsulfoxonium salts.

Examples of particularly preferred compounds of the formula I are given in the tables below:

TABLE A

| $R^1$ | $R^2$ | $R^3$ | $R^4$ | X |
|---|---|---|---|---|
| H | $CH_3$ | H | H | O |
| H | $CH_3CH_2$ | H | H | O |
| H | $CH_3CH_2CH_2$ | H | H | O |
| H | $(CH_3)_2CH$ | H | H | O |
| H | $(CH_3)_3C$ | H | H | O |
| H | $CH_3CH_2CH(CH_3)$ | H | H | O |
| H | $CH_3CH_2CH_2CH_2$ | H | H | O |
| H | $(CH_3)_2CHCH_2$ | H | H | O |
| H | pentyl | H | H | O |
| H | $(CH_3)_2CHCH_2CH_2$ | H | H | O |
| H | $CH_3(CH_2)_2CH(CH_3)$ | H | H | O |
| H | nonyl | H | H | O |
| H | cyclopropyl | H | H | O |
| H | decyl | H | H | O |
| H | 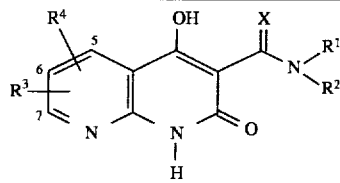 —CH(CH$_3$) | H | H | O |
| H | —(CH$_2$)$_4$— (phenyl) | H | H | O |
| H | $CH_3OCH_2CH(CH_3)$ | H | H | O |

TABLE A-continued

Structure: 1,8-naphthyridine with R⁴ at position 5, R³ at positions 6/7, OH at 4-position, and C(=X)N(R¹)(R²) at 3-position; 2-oxo, 1-H.

| R¹ | R² | R³ | R⁴ | X |
|---|---|---|---|---|
| H | CH₃C(CH₂CH₃)₂ | H | H | O |
| H | (CH₃)₃CCH₂C(CH₃)₂ | H | H | O |
| H | HC≡C—C(CH₃)₂ | H | H | O |
| H | H₂C=CH—C(CH₃)₂ | H | H | O |
| H | [(CH₃)₂CH]₂CH | H | H | O |
| H | cyclopropyl-CH(CH₃) | H | H | O |
| H | cyclopentyl | H | H | O |
| H | cyclohexyl | H | H | O |
| (CH₃CH₂)₂CH | H | H | H | O |
| CH₃SCH₂CH(CH₃) | H | H | H | O |
| CH₃O | H | H | H | O |
| CH₃CH₂O | H | H | H | O |
| (CH₃)₂CHO | H | H | H | O |
| (CH₃)₃CO | H | H | H | O |
| HC≡C—CH(CH₃) | H | H | H | O |
| H₂C=CH—CH(CH₃) | H | H | H | O |
| HC≡C—CH₂ | H | H | H | O |
| H₂C=CH—CH₂ | H | H | H | O |
| CH₃C≡C—CH₂ | H | H | H | O |
| CH₃C≡C—CH(CH₃) | H | H | H | O |
| CH₃CH=CHCH(CH₃) | H | H | H | O |
| (CH₃)₂NCH₂CH(CH₃) | H | H | H | O |
| CH₃CH₂OCH₂CH(CH₃) | H | H | H | O |
| H | phenyl-OCH₂CH(CH₃) | H | H | O |
| CH₃ | (CH₃)₂CH | H | H | O |
| CH₃ | (CH₃)₃C | H | H | O |
| CH₃ | HC≡C—C(CH₃)₂ | H | H | O |
| CH₃CH₂ | CH₃CH₂ | H | H | O |
| CH₃ | CH₃OCH₂CH(CH₃) | H | H | O |
| CH₃CH₂ | phenyl-CH(CH₃) | H | H | O |
| CH₃ | cyclopropyl-CH(CH₃) | H | H | O |
|  | —(CH₂)₃— | H | H | O |
|  | —(CH₂)₄— | H | H | O |
|  | —(CH₂)₅— | H | H | O |
| (CH₃)₂CH | H | 7-CH₃ | H | O |
| (CH₃)₃C | H | 6-Cl | H | O |
| (CH₃)₂CH | H | 6-NO₂ | H | O |
| (CH₃)₃C | H | H | 5-CH₃ | O |
| cyclopropyl-CH(CH₃) | H | 7-CH₃ | H | O |
| HC≡C—C(CH₃)₂ | H | H | 5-OCH₃ | O |
| (CH₃)₂CH | H | 7-Cl | 6-CH₃ | O |
| (CH₃)₃C | H | H | 5-F | O |
| (CH₃)₂CH | H | H | H | S |

TABLE A-continued

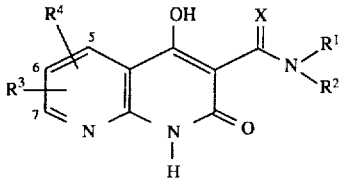

| R¹ | R² | R³ | R⁴ | X |
|---|---|---|---|---|
| $(CH_3)_3C$ | H | H | H | S |
| H | cyclopropyl-CH(CH₃) | H | H | S |
| H | phenyl-CH(CH₃) | H | H | S |
| H | $HC \equiv C-C(CH_3)_2$ | H | H | S |
| H | $CH_3OCH_2CH(CH_3)$ | H | H | S |
| H | $CH_2=CHC(CH_3)_2$ | H | H | S |
| H | cyclopropyl | H | H | S |
| $CH_3$ | $(CH_3)_2CH$ | H | H | S |
| $CH_3CH_2$ | $(CH_3)_2CHCH_2$ | H | H | S |
| $CH_3$ | $CH_3SCH_2CH(CH_3)$ | H | H | S |
| H | $CH_3SCH_2CH(CH_3)$ | H | H | S |
|  | $-(CH_2)_3-$ | H | H | S |
|  | $-(CH_2)_4-$ | H | H | S |
|  | $-(CH_2)_5-$ | H | H | S |
| $CH_3CH_2O$ | H | H | H | S |
| $(CH_3)_2CHO$ | H | H | H | S |
| $(CH_3)_3CO$ | H | H | H | S |
| $(CH_3)_2NCH_2CH(CH_3)$ | H | H | H | S |

TABLE B

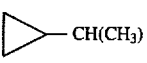

| R¹ | R² | X |
|---|---|---|
| $CH_3$ | H | O |
| $CH_3CH_2$ | H | O |
| $(CH_3)_2CH$ | H | O |
| $(CH_3)_3C$ | H | O |
| cyclopropyl | H | O |
| nonyl | H | O |
| phenyl-CH(CH₃) | H | O |
| $CH_3OCH_2CH(CH_3)$ | H | O |
| cyclopentyl | H | O |
| $HC \equiv CC(CH_3)_2$ | H | O |
| $H_2C=CHC(CH_3)_2$ | H | O |
| cyclopropyl-CH(CH₃) | H | O |
| cyclopropyl | $CH_3$ | O |
| $(CH_3)_2CH$ | $CH_3$ | O |
| $(CH_3)_3C$ | $CH_3$ | O |

TABLE B-continued

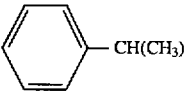

| R¹ | R² | X |
|---|---|---|
| $CH_3SCH_2CH(CH_3)$ | H | O |
| $CH_3$ | H | S |
| $(CH_3)_2CH$ | H | S |
| $(CH_3)_3C$ | H | S |
| cyclopropyl | H | S |
| decyl | H | S |
| phenyl-CH(CH₃) | H | S |
| $CH_3OCH_2CH(CH_3)$ | H | S |
| $CH_3SCH_2CH(CH_3)$ | H | S |
| $HC \equiv CC(CH_3)_2$ | H | S |
| $H_2C=CHC(CH_3)_2$ | H | S |
| $CH_3OCH_2CH(CH_3)$ | H | S |
| $CH_3SCH_2CH(CH_3)$ | H | S |
| $HC \equiv CC(CH_3)_2$ | H | S |
| $H_2C=CHC(CH_3)_2$ | H | S |
| cyclopropyl-CH(CH₃) | H | S |

TABLE B-continued

| R¹ | R² | X |
|---|---|---|
| (CH₃)₂CH | CH₃ | S |
| (CH₃)₃C | CH₃ | S |
| (CH₃)₂CHO | H | O |
| (CH₃)₂NCH₂CH(CH₃) | H | O |
| (CH₃)₃CO | H | O |
| (CH₃)₂CHCH(CH₃) | H | O |

TABLE C

where R¹, R² and X have the meanings given in Table A.

TABLE D

where R¹, R² and X have the meanings given in Table A.

TABLE E

| R¹ | R² | R³ | X |
|---|---|---|---|
| CH₃ | H | H | O |
| CH₃CH₂ | H | H | O |
| (CH₃)₂CH | H | H | O |
| (CH₃)₃C | H | H | O |
| cyclopropyl | H | H | O |
| nonyl | H | H | O |
|  | H | H | O |
| CH₃OCH₂CH(CH₃) | H | H | O |
| cyclopentyl | H | H | O |

TABLE E-continued

| R¹ | R² | R³ | X |
|---|---|---|---|
| HC≡CC(CH₃)₂ | H | H | O |
| H₂C=CHC(CH₃)₂ | H | H | O |
| —CH(CH₃) | H | H | O |
| cyclopropyl | CH₃ | H | O |
| (CH₃)₂CH | CH₃ | H | O |
| (CH₃)₃C | CH₃ | H | O |
| CH₃SCH₂CH(CH₃) | H | H | O |
| (CH₃)₂CH | H | 2-CH₃ | O |
| (CH₃)₃C | H | 2-CH₃ | O |
| —CH(CH₃) | H | 2-CH₃ | O |
| HC≡CC(CH₃)₂ | H | 2-CH₃ | O |
| H₂C=CHC(CH₃)₂ | H | 2-CH₃ | O |
| —CH(CH₃) | H | 2-CH₃ | O |
| (CH₃)₂CH | H | 2-CH₃ | S |
| (CH₃)₃C | H | 2-CH₃ | S |
| —CH(CH₃) | H | 2-CH₃ | S |
| —CH(CH₃) | H | 2-CH₃ | S |
| HC≡CC(CH₃)₂ | H | 2-CH₃ | S |
| H₂C=CHC(CH₃)₂ | H | 2-CH₃ | S |
| CH₃ | H | H | S |
| (CH₃)₂CH | H | H | S |
| (CH₃)₃C | H | H | S |
| cyclopropyl | H | H | S |
| decyl | H | H | S |
| —CH(CH₃) | H | H | S |
| CH₃OCH₂CH(CH₃) | H | H | S |
| CH₃SCH₂CH(CH₃) | H | H | S |
| HC≡CC(CH₃)₂ | H | H | S |
| H₂C=CHC(CH₃)₂ | H | H | S |
| —CH(CH₃) | H | H | S |
| (CH₃)₂CH | CH₃ | H | S |
| (CH₃)₃C | CH₃ | H | S |
| (CH₃)₂CHO | H | H | O |
| (CH₃)₂NCH₂CH(CH₃) | H | H | O |
| (CH₃)₃CO | H | H | O |
| (CH₃)₂CHCH(CH₃) | H | H | O |

TABLE F

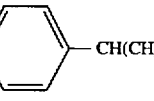

| R¹ | R² | R³ | R⁴ | X |
|---|---|---|---|---|
| CH₃ | H | CH₃ | H | O |
| CH₃CH₂ | H | CH₃ | H | O |
| (CH₃)₂CH | H | CH₃ | H | O |
| (CH₃)₃C | H | CH₃ | H | O |
| cyclopropyl | H | CH₃ | H | O |
| nonyl | H | CH₃ | H | O |
| phenyl—CH(CH₃) | H | CH₃ | H | O |
| CH₃OCH₂CH(CH₃) | H | CH₃ | H | O |
| cyclopentyl | H | CH₃ | H | O |
| HC≡CC(CH₃)₂ | H | CH₃ | H | O |
| H₂C=CHC(CH₃)₂ | H | CH₃ | H | O |
| cyclopropyl—CH(CH₃) | H | CH₃ | H | O |
| cyclopropyl | CH₃ | CH₃ | H | O |
| (CH₃)₂CH | CH₃ | CH₃ | H | O |
| (CH₃)₃C | CH₃ | CH₃ | H | O |
| CH₃SCH₂CH(CH₃) | H | CH₃ | H | O |
| CH₃ | H | CH₃ | H | S |
| (CH₃)₂CH | H | CH₃ | H | S |
| (CH₃)₃C | H | CH₃ | H | S |
| cyclopropyl | H | CH₃ | H | S |
| decyl | H | CH₃ | H | S |
| phenyl—CH(CH₃) | H | CH₃ | H | S |
| CH₃OCH₂CH(CH₃) | H | CH₃ | H | S |
| CH₃SCH₂CH(CH₃) | H | CH₃ | H | S |
| HC≡CC(CH₃)₂ | H | CH₃ | H | S |
| H₂C=CHC(CH₃)₂ | H | CH₃ | H | S |
| cyclopropyl—CH(CH₃) | H | CH₃ | H | S |
| (CH₃)₂CH | CH₃ | CH₃ | H | S |
| (CH₃)₃C | CH₃ | CH₃ | H | S |
| (CH₃)₂CHO | H | CH₃ | H | O |
| (CH₃)₂NCH₂CH(CH₃) | H | CH₃ | H | O |
| (CH₃)₃CO | H | CH₃ | H | O |
| (CH₃)₂CHCH(CH₃) | H | CH₃ | H | O |
| (CH₃)₂CH | H | C₆H₅ | H | O |
| (CH₃)₃C | H | C₆H₅ | H | O |
| cyclopropyl—CH(CH₃) | H | C₆H₅ | H | O |
| phenyl—CH(CH₃) | H | C₆H₅ | H | O |
| HC≡CC(CH₃)₂ | H | C₆H₅ | H | O |
| H₂C=CHC(CH₃)₂ | H | C₆H₅ | H | O |
| (CH₃)₂CH | H | CH₃ | CH₃ | O |
| (CH₃)₃C | H | CH₃ | CH₃ | O |

TABLE F-continued

| R¹ | R² | R³ | R⁴ | X |
|---|---|---|---|---|
| cyclopropyl—CH(CH₃) | H | CH₃ | CH₃ | O |
| phenyl—CH(CH₃) | H | CH₃ | CH₃ | O |
| HC≡CC(CH₃)₂ | H | CH₃ | CH₃ | O |
| H₂C=CHC(CH₃)₂ | H | CH₃ | CH₃ | O |

TABLE G

| R¹ | R² | X |
|---|---|---|
| CH₃ | H | O |
| CH₃CH₂ | H | O |
| (CH₃)₂CH | H | O |
| (CH₃)₃C | H | O |
| cyclopropyl | H | O |
| nonyl | H | O |
| phenyl—CH(CH₃) | H | O |
| CH₃OCH₂CH(CH₃) | H | O |
| cyclopentyl | H | O |
| HC≡CC(CH₃)₂ | H | O |
| H₂C=CHC(CH₃)₂ | H | O |
| cyclopropyl—CH(CH₃) | H | O |
| cyclopropyl | CH₃ | O |
| (CH₃)₂CH | CH₃ | O |
| (CH₃)₃C | CH₃ | O |
| CH₃SCH₂CH(CH₃) | H | O |
| CH₃ | H | S |
| (CH₃)₂CH | H | S |
| (CH₃)₃C | H | S |
| cyclopropyl | H | S |
| decyl | H | S |
| phenyl—CH(CH₃) | H | S |
| CH₃OCH₂CH(CH₃) | H | S |
| CH₃SCH₂CH(CH₃) | H | S |

TABLE G-continued

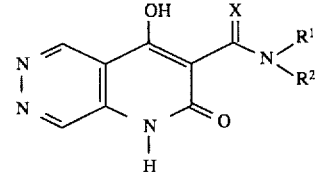

| R¹ | R² | X |
|---|---|---|
| HC≡CC(CH₃)₂ | H | S |
| H₂C=CHC(CH₃)₂ | H | S |
| cyclopropyl-CH(CH₃) | H | S |
| (CH₃)₂CH | CH₃ | S |
| (CH₃)₃C | CH₃ | S |
| (CH₃)₂CHO | H | O |
| (CH₃)₂NCH₂CH(CH₃) | H | O |
| (CH₃)₃CO | H | O |
| (CH₃)₂CHCH(CH₃) | H | O |

TABLE H

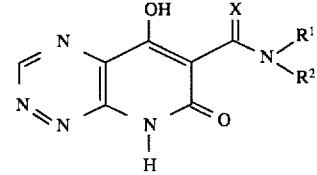

where R¹, R² and X have the meanings given in Table G.

TABLE I

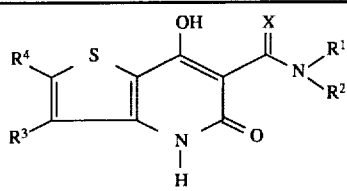

where R¹, R² and X have the meanings given in Table G.

TABLE J

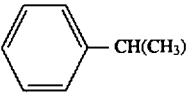

| R¹ | R² | R³ | R⁴ | X |
|---|---|---|---|---|
| H | CH₃ | H | H | O |
| H | CH₃CH₂ | H | H | O |
| H | CH₃CH₂CH₂ | H | H | O |
| H | (CH₃)₂CH | H | H | O |
| H | (CH₃)₃C | H | H | O |
| H | CH₃CH₂CH(CH₃) | H | H | O |
| H | CH₃CH₂CH₂CH₂ | H | H | O |
| H | (CH₃)₂CHCH₂ | H | H | O |
| H | pentyl | H | H | O |
| H | (CH₃)₂CHCH₂CH₂ | H | H | O |
| H | CH₃(CH₂)₂CH(CH₃) | H | H | O |
| H | nonyl | H | H | O |
| H | cyclopropyl | H | H | O |
| H | decyl | H | H | O |
| H | phenyl-CH(CH₃) | H | H | O |
| H | phenyl-(CH₂)₄ | H | H | O |
| H | CH₃OCH₂CH(CH₃) | H | H | O |
| H | CH₃C(CH₂CH₃)₂ | H | H | O |
| H | (CH₃)₃CCH₂C(CH₃)₂ | H | H | O |
| H | HC≡C—C(CH₃)₂ | H | H | O |
| H | H₂C=CH—C(CH₃)₂ | H | H | O |
| H | [(CH₃)₂CH]₂CH | H | H | O |

TABLE J-continued

[Structure: Thieno-fused pyridinone with R⁴ and R³ on thiophene ring, OH, C(=X)N(R¹)(R²) substituent, and NH in pyridinone ring]

| R¹ | R² | R³ | R⁴ | X |
|---|---|---|---|---|
| H | ▷—CH(CH₃) | H | H | O |
| H | cyclopentyl | H | H | O |
| H | cyclohexyl | H | H | O |
| (CH₃CH₂)₂CH | H | H | H | O |
| CH₃SCH₂CH(CH₃) | H | H | H | O |
| CH₃O | H | H | H | O |
| CH₃CH₂O | H | H | H | O |
| (CH₃)₂CHO | H | H | H | O |
| (CH₃)₃CO | H | H | H | O |
| HC≡C—CH(CH₃) | H | H | H | O |
| H₂C=CH—CH(CH₃) | H | H | H | O |
| HC≡C—CH₂ | H | H | H | O |
| H₂C=CH—CH₂ | H | H | H | O |
| CH₃C≡C—CH₂ | H | H | H | O |
| CH₃C≡C—CH(CH₃) | H | H | H | O |
| CH₃CH=CHCH(CH₃) | H | H | H | O |
| (CH₃)₂NCH₂CH(CH₃) | H | H | H | O |
| CH₃CH₂OCH₂CH(CH₃) | H | H | H | O |
| H | C₆H₅—OCH₂CH(CH₃) | H | H | O |
| CH₃ | (CH₃)₂CH | H | H | O |
| CH₃ | (CH₃)₃C | H | H | O |
| CH₃ | HC≡C—C(CH₃)₂ | H | H | O |
| CH₃CH₂ | CH₃CH₂ | H | H | O |
| CH₃ | CH₃OCH₂CH(CH₃) | H | H | O |
| CH₃CH₂ | C₆H₅—CH(CH₃) | H | H | O |
| CH₃ | ▷—CH(CH₃) | H | H | O |
|  | —(CH₂)₃— | H | H | O |
|  | —(CH₂)₄— | H | H | O |
|  | —(CH₂)₅— | H | H | O |
| (CH₃)₂CH | H | NO₂ | H | O |
| (CH₃)₃C | H | NO₂ | H | O |
| (CH₃)₂CH | H | CN | CH₃ | O |
| (CH₃)₃C | H | CN | CH₃ | O |
| ▷—CH(CH₃) | H | H | CH₃ | O |
| HC≡C—C(CH₃)₂ | H | H | CH₃ | O |
| (CH₃)₂CH | H | H | CH₃ | O |
| (CH₃)₃C | H | H | CH₃ | O |
| (CH₃)₂CH | H | H | H | S |
| (CH₃)₃C | H | H | H | S |
| H | ▷—CH(CH₃) | H | H | S |

TABLE J-continued

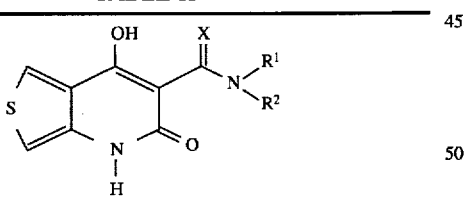

| R¹ | R² | R³ | R⁴ | X |
|---|---|---|---|---|
| H | —CH(CH₃) (phenyl) | H | H | S |
| H | HC≡C—C(CH₃)₂ | H | H | S |
| H | CH₃OCH₂CH(CH₃) | H | H | S |
| H | CH₂=CHC(CH₃)₂ | H | H | S |
| H | cyclopropyl | H | H | S |
| CH₃ | (CH₃)₂CH | H | H | S |
| CH₃CH₂ | (CH₃)₂CHCH₂ | H | H | S |
| CH₃ | CH₃SCH₂CH(CH₃) | H | H | S |
| H | CH₃SCH₂CH(CH₃) | H | H | S |
|  | —(CH₂)₃— | H | H | S |
|  | —(CH₂)₄— | H | H | S |
|  | —(CH₂)₅— | H | H | S |
| CH₃CH₂O | H | H | H | S |
| (CH₃)₂CHO | H | H | H | S |
| (CH₃)₃CO | H | H | H | S |
| (CH₃)₂NCH₂CH(CH₃) | H | H | H | S |
| (CH₃)₂CH | H |  | —(CH₂)₄— | O |
| (CH₃)₃C | H |  | —(CH₂)₄— | O |
| cyclopropyl-CH(CH₃) | H |  | —(CH₂)₄— | O |
| phenyl-CH(CH₃) | H |  | —(CH₂)₄— | O |
| HC≡CC(CH₃)₂ | H |  | —(CH₂)₄— | O |
| H₂C=CHC(CH₃)₂ | H |  | —(CH₂)₄— | O |

TABLE K

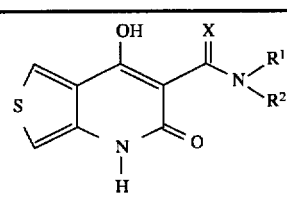

| R¹ | R² | X |
|---|---|---|
| H | CH₃ | O |
| H | CH₃CH₂ | O |
| H | CH₃CH₂CH₂ | O |
| H | (CH₃)₂CH | O |
| H | (CH₃)₃C | O |
| H | CH₃CH₂CH(CH₃) | O |
| H | CH₃CH₂CH₂CH₂ | O |
| H | (CH₃)₂CHCH₂ | O |
| H | pentyl | O |
| H | (CH₃)₂CHCH₂CH₂ | O |
| H | CH₃(CH₂)₂CH(CH₃) | O |
| H | nonyl | O |
| H | cyclopropyl | O |
| H | decyl | O |
| H | phenyl-CH(CH₃) | O |
| H | phenyl-(CH₂)₄ | O |
| H | CH₃OCH₂CH(CH₃) | O |
| H | CH₃C(CH₂CH₃)₂ | O |
| H | (CH₃)₃CCH₂C(CH₃)₂ | O |
| H | HC≡C—C(CH₃)₂ | O |

TABLE K-continued

| R¹ | R² | X |
|---|---|---|
| H | H₂C=CH—C(CH₃)₂ | O |
| H | [(CH₃)₂CH]₂CH | O |
| H | ▷—CH(CH₃) | O |
| H | cyclopentyl | O |
| H | cyclohexyl | O |
| (CH₃CH₂)₂CH | H | O |
| CH₃SCH₂CH(CH₃) | H | O |
| CH₃O | H | O |
| CH₃CH₂O | H | O |
| (CH₃)₂CHO | H | O |
| (CH₃)₃CO | H | O |
| HC≡C—CH(CH₃) | H | O |
| H₂C=CH—CH(CH₃) | H | O |
| HC≡C—CH₂ | H | O |
| H₂C=CH—CH₂ | H | O |
| CH₃C≡C—CH₂ | H | O |
| CH₃C≡C—CH(CH₃) | H | O |
| CH₃CH=CHCH(CH₃) | H | O |
| (CH₃)₂NCH₂CH(CH₃) | H | O |
| CH₃CH₂OCH₂CH(CH₃) | H | O |
| H | Ph—OCH₂CH(CH₃) | O |
| CH₃ | (CH₃)₂CH | O |
| CH₃ | (CH₃)₃C | O |
| CH₃ | HC≡C—C(CH₃)₂ | O |
| CH₃CH₂ | CH₃CH₂ | O |
| CH₃ | CH₃OCH₂CH(CH₃) | O |
| CH₃CH₂ | Ph—CH(CH₃) | O |

TABLE K-continued

| R¹ | R² | X |
|---|---|---|
| CH₃ | ▷—CH(CH₃) | O |
|  | —(CH₂)₃— | O |
|  | —(CH₂)₄— | O |
|  | —(CH₂)₅— | O |
| (CH₃)₂CH | H | S |
| (CH₃)₃C | H | S |
| H | ▷—CH(CH₃) | S |
| H | Ph—CH(CH₃) | S |
| H | HC≡C—C(CH₃)₂ | S |
| H | CH₃OCH₂CH(CH₃) | S |
| H | CH₂=CHCH(CH₃)₂ | S |
| H | cyclopropyl | S |
| CH₃ | (CH₃)₂CH | S |
| CH₃CH₂ | (CH₃)₂CHCH₂ | S |
| CH₃ | CH₃SCH₂CH(CH₃) | S |
| H | CH₃SCH₂CH(CH₃) | S |
| —(CH₂)₃— |  | S |
|  | —(CH₂)₄— | S |
|  | —(CH₂)₅— | S |
| CH₃CH₂O | H | S |
| (CH₃)₂CHO | H | S |
| (CH₃)₃CO | H | S |
| (CH₃)₂NCH₂CH(CH₃) | H | S |

TABLE L

| R¹ | R² | R³ | R⁴ | X |
|---|---|---|---|---|
| H | CH₃ | H | H | O |
| H | CH₃CH₂ | H | H | O |
| H | CH₃CH₂CH₂ | H | H | O |
| H | (CH₃)₂CH | H | H | O |
| H | (CH₃)₃C | H | H | O |
| H | CH₃CH₂CH(CH₃) | H | H | O |
| H | CH₃CH₂CH₂CH₂ | H | H | O |

TABLE L-continued

| R¹ | R² | R³ | R⁴ | X |
|---|---|---|---|---|
| H | (CH₃)₂CHCH₂ | H | H | O |
| H | pentyl | H | H | O |
| H | (CH₃)₂CHCH₂CH₂ | H | H | O |
| H | CH₃(CH₂)₂CH(CH₃) | H | H | O |
| H | nonyl | H | H | O |
| H | cyclopropyl | H | H | O |
| H | decyl | H | H | O |
| H | C₆H₅—CH(CH₃) | H | H | O |
| H | C₆H₅—(CH₂)₄ | H | H | O |
| H | CH₃OCH₂CH(CH₃) | H | H | O |
| H | CH₃C(CH₂CH₃)₂ | H | H | O |
| H | (CH₃)₃CCH₂C(CH₃)₂ | H | H | O |
| H | HC≡C—C(CH₃)₂ | H | H | O |
| H | H₂C=CH—C(CH₃)₂ | H | H | O |
| H | [(CH₃)₂CH]₂CH | H | H | O |
| H | cyclopropyl—CH(CH₃) | H | H | O |
| H | cyclopentyl | H | H | O |
| H | cyclohexyl | H | H | O |
| (CH₃CH₂)₂CH | H | H | H | O |
| CH₃SCH₂CH(CH₃) | H | H | H | O |
| CH₃O | H | H | H | O |
| CH₃CH₂O | H | H | H | O |
| (CH₃)₂CHO | H | H | H | O |
| (CH₃)₃CO | H | H | H | O |
| HC≡C—CH(CH₃) | H | H | H | O |
| H₂C=CH—CH(CH₃) | H | H | H | O |
| HC≡C—CH₂ | H | H | H | O |
| H₂C=CH—CH₂ | H | H | H | O |
| CH₃C≡C—CH₂ | H | H | H | O |
| CH₃C≡C—CH(CH₃) | H | H | H | O |
| CH₃CH=CHCH(CH₃) | H | H | H | O |
| (CH₃)₂NCH₂CH(CH₃) | H | H | H | O |
| CH₃CH₂OCH₂CH(CH₃) | H | H | H | O |
| H | C₆H₅—OCH₂CH(CH₃) | H | H | O |
| CH₃ | (CH₃)₂CH | H | H | O |
| CH₃ | (CH₃)₃C | H | H | O |
| CH₃ | HC≡C—C(CH₃)₂ | H | H | O |
| CH₃CH₂ | CH₃CH₂ | H | H | O |
| CH₃ | CH₃OCH₂CH(CH₃) | H | H | O |
| CH₃CH₂ | C₆H₅—CH(CH₃) | H | H | O |

TABLE L-continued

[Structure: thieno-pyridine with OH, R⁴, R³, S, NH, =O, and C(=X)N(R¹)(R²) substituents]

| R¹ | R² | R³ | R⁴ | X |
|---|---|---|---|---|
| CH₃ | cyclopropyl-CH(CH₃) | H | H | O |
|  | —(CH₂)₃— |  | H | O |
|  | —(CH₂)₄— |  | H | O |
|  | —(CH₂)₅— |  | H | O |
| (CH₃)₂CH | H | CO₂CH₂CH₃ | CH₃ | O |
| (CH₃)₃C | H | CO₂CH₂CH₃ | CH₃ | O |
| (CH₃)₂CH | H | CH₃ | H | O |
| (CH₃)₃C | H | CH₃ | H | O |
| cyclopropyl-CH(CH₃) | H | CH₃ | H | O |
| HC≡C—C(CH₃)₂ | H | CH₃ | H | O |
| (CH₃)₂CH | H | H | CH₃ | O |
| (CH₃)₃C | H | H | CH₃ | O |
| (CH₃)₂CH | H | H | H | S |
| (CH₃)₃C | H | H | H | S |
| H | cyclopropyl-CH(CH₃) | H | H | S |
| H | phenyl-CH(CH₃) | H | H | S |
| H | HC≡C—C(CH₃)₂ | H | H | S |
| H | CH₃OCH₂CH(CH₃) | H | H | S |
| H | CH₂=CHC(CH₃)₂ | H | H | S |
| H | cyclopropyl | H | H | S |
| CH₃ | (CH₃)₂CH | H | H | S |
| CH₃CH₂ | (CH₃)₂CHCH₂ | H | H | S |
| CH₃ | CH₃SCH₂CH(CH₃) | H | H | S |
| H | CH₃SCH₂CH(CH₃) | H | H | S |
|  | —(CH₂)₃— |  | H | S |
|  | —(CH₂)₄— |  | H | S |
|  | —(CH₂)₅— |  | H | S |
| CH₃CH₂O | H | H | H | S |
| (CH₃)₂CHO | H | H | H | S |
| (CH₃)₃CO | H | H | H | S |
| (CH₃)₂NCH₂CH(CH₃) | H | H | H | S |
| (CH₃)₂CH | H |  | —(CH₂)₄— | O |
| (CH₃)₃C | H |  | —(CH₂)₄— | O |
| cyclopropyl-CH(CH₃) | H |  | —(CH₂)₄— | O |
| phenyl-CH(CH₃) | H |  | —(CH₂)₄— | O |
| HC≡CC(CH₃)₂ | H |  | —(CH₂)₄— | O |
| H₂C=CHC(CH₃)₂ | H |  | —(CH₂)₄— | O |

TABLE M

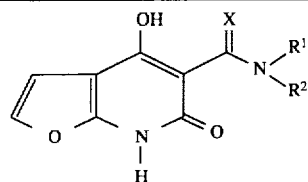

| R¹ | R² | X |
|---|---|---|
| XCH₃ | H | O |
| CH₃CH₂ | H | O |
| (CH₃)₂CH | H | O |
| (CH₃)₃C | H | O |
| cyclopropyl | H | O |
| nonyl | H | O |
| phenyl-CH(CH₃) | H | O |
| CH₃OCH₂CH(CH₃) | H | O |
| cyclopentyl | H | O |
| HC≡CC(CH₃)₂ | H | O |
| H₂C=CHC(CH₃)₂ | H | O |
| cyclopropyl-CH(CH₃) | H | O |
| cyclopropyl | CH₃ | O |
| (CH₃)₂CH | CH₃ | O |
| (CH₃)₃C | CH₃ | O |
| CH₃SCH₂CH(CH₃) | H | O |
| CH₃ | H | S |
| (CH₃)₂CH | H | S |
| (CH₃)₃C | H | S |
| cyclopropyl | H | S |
| decyl | H | S |
| phenyl-CH(CH₃) | H | S |
| CH₃OCH₂CH(CH₃) | H | S |
| CH₃SCH₂CH(CH₃) | H | S |
| HC≡CC(CH₃)₂ | H | S |
| H₂C=CHC(CH₃)₂ | H | S |
| cyclopropyl-CH(CH₃) | H | S |
| (CH₃)₂CH | CH₃ | S |
| (CH₃)₃C | CH₃ | S |
| (CH₃)₂CHO | H | O |
| (CH₃)₂NCH₂CH(CH₃) | H | O |
| (CH₃)₃CO | H | O |
| (CH₃)₂CHCH(CH₃) | H | O |

TABLE N

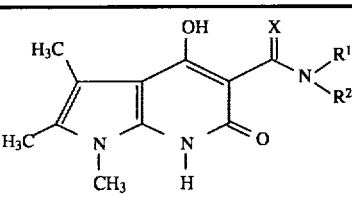

where R¹, R² and X have the meanings given in Table M.

TABLE O

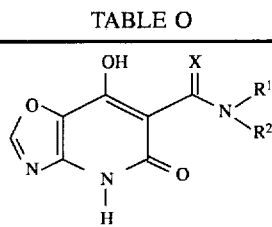

| R¹ | R² | X |
|---|---|---|
| CH₃ | H | O |
| CH₃CH₂ | H | O |
| (CH₃)₂CH | H | O |
| (CH₃)₃C | H | O |
| cyclopropyl | H | O |
| nonyl | H | O |
| phenyl-CH(CH₃) | H | O |
| CH₃OCH₂CH(CH₃) | H | O |
| cyclopentyl | H | O |
| HC≡CC(CH₃)₂ | H | O |
| H₂C=CHC(CH₃)₂ | H | O |
| cyclopropyl-CH(CH₃) | H | O |
| cyclopropyl | CH₃ | O |
| (CH₃)₂CH | CH₃ | O |
| (CH₃)₃C | CH₃ | O |
| CH₃SCH₂CH(CH₃) | H | O |
| CH₃ | H | S |
| (CH₃)₂CH | H | S |
| (CH₃)₃C | H | S |
| cyclopropyl | H | S |
| decyl | H | S |
| cyclopropyl-CH(CH₃) | H | S |
| CH₃OCH₂CH(CH₃) | H | S |
| CH₃SCH₂CH(CH₃) | H | S |
| HC≡CC(CH₃)₂ | H | S |
| H₂C=CHC(CH₃)₂ | H | S |
| cyclopropyl-CH(CH₃) | H | S |
| (CH₃)₂CH | CH₃ | S |
| (CH₃)₃C | CH₃ | S |
| (CH₃)₂CHO | H | O |
| (CH₃)₂NCH₂CH(CH₃) | H | O |
| (CH₃)₃CO | H | O |
| (CH₃)₂CHCH(CH₃) | H | O |

TABLE P

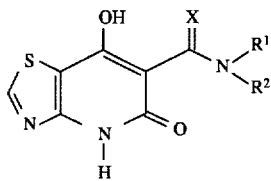

where R¹, R² and X have the meanings given in Table O.

TABLE Q

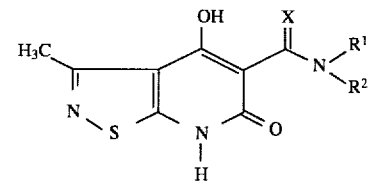

| R¹ | R² | X |
|---|---|---|
| CH₃ | H | O |
| CH₃CH₂ | H | O |
| (CH₃)₂CH | H | O |
| (CH₃)₃C | H | O |
| cyclopropyl | H | O |
| nonyl | H | O |
| phenyl-CH(CH₃) | H | O |
| CH₃OCH₂CH(CH₃) | H | O |
| cyclopentyl | H | O |
| HC≡CC(CH₃)₂ | H | O |
| H₂C=CHC(CH₃)₂ | H | O |
| cyclopropyl-CH(CH₃) | H | O |
| cyclopropyl | CH₃ | O |
| (CH₃)₂CH | CH₃ | O |
| (CH₃)₃C | CH₃ | O |
| CH₃SCH₂CH(CH₃) | H | O |
| CH₃ | H | S |
| (CH₃)₂CH | H | S |
| (CH₃)₃C | H | S |
| cyclopropyl | H | S |
| decyl | H | S |
| phenyl-CH(CH3) | H | S |
| CH₃OCH₂CH(CH₃) | H | S |
| CH₃SCH₂CH(CH₃) | H | S |
| HC≡CC(CH₃)₂ | H | S |
| H₂C=CHC(CH₃)₂ | H | S |
| cyclopropyl-CH(CH₃) | H | S |
| (CH₃)₂CH | CH₃ | S |
| (CH₃)₃C | CH₃ | S |
| (CH₃)₂CHO | H | O |
| (CH₃)₂NCH₂CH(CH₃) | H | O |
| (CH₃)₃CO | H | O |
| (CH₃)₂CHCH(CH₃) | H | O |

TABLE R

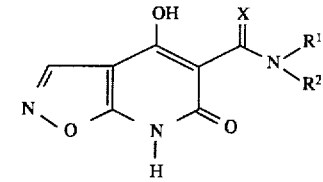

where R¹, R² and X have the meanings given in Table O.

TABLE S

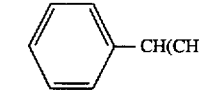

where R¹, R² and X have the meanings given in Table Q.

TABLE T

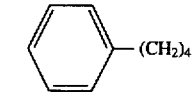

| R¹ | R² | X |
|---|---|---|
| H | CH₃ | O |
| H | CH₃CH₂ | O |
| H | CH₃CH₂CH₂ | O |
| H | (CH₃)₂CH | O |
| H | (CH₃)₃C | O |
| H | CH₃CH₂CH(CH₃) | O |
| H | CH₃CH₂CH₂CH₂ | O |
| H | (CH₃)₂CHCH₂ | O |
| H | pentyl | O |
| H | (CH₃)₂CHCH₂CH₂ | O |
| H | CH₃(CH₂)₂CH(CH₃) | O |
| H | nonyl | O |
| H | cyclopropyl | O |
| H | decyl | O |
| H | phenyl-CH(CH₃) | O |
| H | phenyl-(CH₂)₄ | O |
| H | CH₃OCH₂CH(CH₃) | O |
| H | CH₃C(CH₂CH₃)₂ | O |
| H | (CH₃)₃CCH₂C(CH₃)₂ | O |
| H | HC≡C—C(CH₃)₂ | O |
| H | H₂C=CH—C(CH₃)₂ | O |
| H | [(CH₃)₂CH]₂CH | O |
| H | cyclopropyl-CH(CH₃) | O |
| H | cyclopentyl | O |
| H | cyclohexyl | O |
| (CH₃CH₂)₂CH | H | O |
| CH₃SCH₂CH(CH₃) | H | O |
| CH₃O | H | O |
| CH₃CH₂O | H | O |
| (CH₃)₂CHO | H | O |
| (CH₃)₃CO | H | O |
| HC≡C—CH(CH₃) | H | O |
| H₂C=CH—CH(CH₃) | H | O |
| HC≡C—CH₂ | H | O |
| H₂C=CH—CH₂ | H | O |
| CH₃C≡C—CH₂ | H | O |

TABLE T-continued

[Structure: isoxazolo-pyridinone with OH, C(=X)NR¹R² substituents]

where R¹, R² and X have meanings as indicated.

| R¹ | R² | X |
|---|---|---|
| CH₃C≡C—CH(CH₃) | H | O |
| CH₃CH=CHCH(CH₃) | H | O |
| (CH₃)₂NCH₂CH(CH₃) | H | O |
| CH₃CH₂OCH₂CH(CH₃) | H | O |
| H | C₆H₄—OCH₂CH(CH₃) | O |
| CH₃ | (CH₃)₂CH | O |
| CH₃ | (CH₃)₃C | O |
| CH₃ | HC≡C—C(CH₃)₂ | O |
| CH₃CH₂ | CH₃CH₂ | O |
| CH₃ | CH₃OCH₂CH(CH₃) | O |
| CH₃CH₂ | C₆H₄—CH(CH₃) | O |
| CH₃ | cyclopropyl-CH(CH₃) | O |
|  | —(CH₂)₃— | O |
|  | —(CH₂)₄— | O |
|  | —(CH₂)₅— | O |
| (CH₃)₂CH | H | S |
| (CH₃)₃C | H | S |
| H | cyclopropyl-CH(CH₃) | S |
| H | cyclopropyl-CH(CH₃) | S |
| H | HC≡C—C(CH₃)₂ | S |
| H | CH₃OCH₂CH(CH₃) | S |
| H | CH₂=CHC(CH₃)₂ | S |
| H | cyclopropyl | S |
| CH₃ | (CH₃)₂CH | S |
| CH₃CH₂ | (CH₃)₂CHCH₂ | S |
| CH₃ | CH₃SCH₂CH(CH₃) | S |
| H | CH₃SCH₂CH(CH₃) | S |
|  | —(CH₂)₃— | S |
|  | —(CH₂)₄— | S |
|  | —(CH₂)₅— | S |
| CH₃CH₂O | H | S |
| (CH₃)₂CHO | H | S |
| (CH₃)₃CO | H | S |
| (CH₃)₂NCH₂CH(CH₃) | H | S |

TABLE U

[Structure: pyrazolo-pyridinone with OH, C(=X)NR¹R², and H₃C—N]

where R¹, R² and X have the meanings given in Table T.

TABLE V

[Structure: pyrrolo-pyridinone with OH, C(=X)NR¹R², and CH₃—N]

where R¹, R² and X have the meanings given in Table T.

TABLE W

[Structure: triazolo-pyridinone with OH, C(=X)NR¹R², and H₃C—N]

| R¹ | R² | X |
|---|---|---|
| CH₃ | H | O |
| CH₃CH₂ | H | O |
| (CH₃)₂CH | H | O |
| (CH₃)₃C | H | O |
| cyclopropyl | H | O |
| nonyl | H | O |
| C₆H₄—CH(CH₃) | H | O |
| CH₃OCH₂CH(CH₃) | H | O |
| cyclopentyl | H | O |
| HC≡CC(CH₃)₂ | H | O |
| H₂C=CHC(CH₃)₂ | H | O |
| cyclopropyl-CH(CH₃) | H | O |
| cyclopropyl | CH₃ | O |
| (CH₃)₂CH | CH₃ | O |
| (CH₃)₃C | CH₃ | O |
| CH₃SCH₂CH(CH₃) | H | O |
| CH₃ | H | S |
| (CH₃)₂CH | H | S |
| (CH₃)₃C | H | S |
| cyclopropyl | H | S |
| decyl | H | S |
| cyclopropyl-CH(CH₃) | H | S |
| CH₃OCH₂CH(CH₃) | H | S |
| CH₃SCH₂CH(CH₃) | H | S |
| HC≡CC(CH₃)₂ | H | S |
| H₂C=CHC(CH₃)₂ | H | S |
| cyclopropyl-CH(CH₃) | H | S |
| (CH₃)₂CH | CH₃ | S |
| (CH₃)₃C | CH₃ | S |

TABLE W-continued

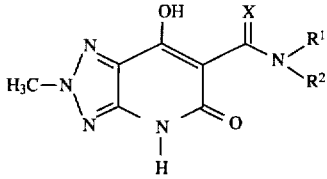

| R¹ | R² | X |
| --- | --- | --- |
| (CH₃)₂CHO | H | O |
| (CH₃)₂NCH₂CH(CH₃) | H | O |
| (CH₃)₃CO | H | O |
| (CH₃)₂CHCH(CH₃) | H | O |

TABLE X

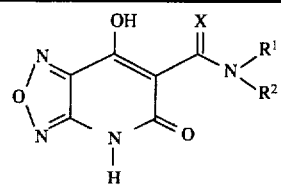

where R¹, R² and X have the meanings given in Table W.

TABLE Y

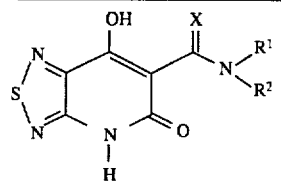

where R¹, R² and X have the meanings given in Table W.

The heterocycles Q listed in the above tables are independent of the meaning of X, or the substituents R¹ and R² are to be considered to be particularly preferred in formula I.

The compounds I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of 90 to 100, and preferably from 95 to 100, % (according to the NMR spectra).

The compounds I according to the invention may be formulated for example as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 3.002 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3.003 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3.012 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3.013 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3.004 is intimately mixed with 97 parts by weight of particulate kaolin. A dust is obtained containing 3% by weight of the active ingredient.

VII. 30 parts by weight of compound no. 3.009 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 3.002 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the compounds according to the invention or agents containing them may be used in a large number of crops for combating unwanted plants. Those which follow are given by way of example:

| | |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea canephora*, *Coffea liberica*) | coffee plants |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | wheat |
| *Vitis vinifera* | grapes |
| *Zea mays* | Indian corn, sweet corn, maize |

To increase the spectrum of action and to achieve synergistic effects, the hydroxypyridonecarboxamides I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, sulfonylureas, (hetero)-aryloxyphenoxypropionic acids and salts, esters, amides thereof, etc.

It may also be useful to apply the novel compounds I, either alone or in combination with other herbicides, in admixture with other crop protection agents, e.g., agents for combating pests or phytopathogenic fungi or bacteria. The compounds may also be mixed with solutions of mineral

SYNTHESIS EXAMPLES

Example 1

6-[(1,1-Dimethylethyl-)aminocarbonyl-]-7-hydroxy-thieno[3,2-b]pyridin-5-(4H)-one (No. 3.002 in Table 3)

3.1 g (13 mmol) of 6-ethoxycarbonyl-7-hydroxy-thieno[3,2-b]pyridin-5(4H)-one and 1.14 g (1.2 eq.) of tert.-butylamine in 80 ml EtOH were stirred for 8 hours at 150° C. in an autoclave. The solvent was removed and the solid residue was stirred with diethyl ether/acetone/ethanol (1/1/1). The crystals were filtered off, washed with diethyl ether and dried.

Yield: 1.3 g (38%), mp 270°–271° C.

Example 2

6- [(1,1-Dimethylpropinyl-)aminocarbonyl-]-7-hydroxy-thieno[3,2-b]pyridin-5(4H)-one (No. 3.012 in Table 3)

3.1 g (13 mmol) of 6-ethoxycarbonyl-7-hydroxy-thieno[3,2-b]pyridin-5(4H)-one and 1.3 g (1.2 eq.) of 1,1-dimethylpropargylamine in 80 ml of EtOH were stirred for 8 hours at 150° C. in an autoclave. The solvent was removed under reduced pressure and the solid residue was stirred with diethyl ether. The solid was filtered off and purified chromatographically (silica gel, methylene chloride/methanol= 8/1).

Yield: 0.4 g (11%), mp 206°–208° C.

Further compounds of the formula I were prepared analogously with appropriate modifications of the starting materials. The compounds thus obtained are listed in the tables below with their physical data.

TABLE 1

| No. | X | Y | R | mp [°C.] |
|---|---|---|---|---|
| 1.001 | N | CH | C(CH₃)₃ | >300 |
| 1.002 | N | CH | CH(CH₃)₂ | 280 |
| 1.003 | N | CH | cyclopropyl | >300 |
| 1.004 | N | CH | nonyl | 200–210 |
| 1.005 | N | CH | CH(CH₃)C₆H₅ | 241–246 |
| 1.006 | N | CH | CH(CH₃)CH₂OCH₃ | 209–212 |
| 1.007 | CH | N | C(CH₃)₃ | 238–241 |
| 1.008 | CH | N | CH(CH₃)₂ | 225–230 |
| 1.009 | CH | N | cyclopropyl | 162–166 |
| 1.010 | CH | N | nonyl | 140–150 |
| 1.011 | CH | N | CH(CH₃)CH₂OCH₃ | 145–155 |
| 1.012 | CH | N | CH(CH₃)—△ | 185–190 |
| 1.013 | CH | N | CH(CH₃)C₆H₅ | 224–226 |
| 1.014 | CH | N | C(CH₂CH₃)₂CH₃ | 196–203 |
| 1.015 | CH | N | C(CH₃)₂CH₂C(CH₃)₃ | 170 |
| 1.016 | CH | N | CH₂CH₂CH₂CH₂—C₆H₅ | 296–300 |
| 1.017 | CH | N | CH[CH(CH₃)₂]₂ | >300 |
| 1.018 | CH | N | C(CH₃)₂CH=CH₂ | 224–226 |

TABLE 2

| No. | R' | R" | R | mp [°C.] |
|---|---|---|---|---|
| 2.001 | —(CH₂)₄— | | CH(CH₃)₂ | >300 |
| 2.002 | —(CH₂)₄— | | decyl | 140–143 |
| 2.003 | —(CH₂)₄— | | cyclopropyl | >300 |
| 2.004 | —(CH₂)₄— | | C(CH₃)₃ | 295–296 |
| 2.005 | CO₂C₂H₅ | CH₃ | C(CH₃)₃ | 273–280 |
| 2.006 | CO₂C₂H₅ | CH₃ | CH(CH₃)₂ | 241–243 |
| 2.007 | CO₂C₂H₅ | CH₃ | cyclopropyl | 258–261 |
| 2.008 | CO₂C₂H₅ | CH₃ | decyl | 125–128 |

TABLE 3

| No. | R' | R" | R | mp [°C.] |
|---|---|---|---|---|
| 3.001 | CN | CH₃ | C(CH₃)₃ | 233–237 |
| 3.002 | H | H | C(CH₃)₃ | 270–271 |
| 3.003 | H | H | CH(CH₃)₂ | 253–256 |
| 3.004 | H | H | cyclopropyl | 274–278 |
| 3.005 | H | H | decyl | 124–126 |
| 3.006 | H | H | nonyl | 120–122 |
| 3.007 | H | H | CH(CH₃)C₆H₅ | 222–223 |
| 3.008 | H | H | CH₂CH₂CH₂CH₂C₆H₅ | 190–191 |
| 3.009 | H | H | CH(CH₃)CH₂OCH₃ | 211–212 |
| 3.010 | H | H | C(CH₂CH₃)₂CH₃ | 223–225 |
| 3.011 | H | H | C(CH₃)₂CH₂C(CH₃)₃ | 190–192 |
| 3.012 | H | H | C(CH₃)₂C≡CH | 206–208 |
| 3.013 | H | H | CH(CH₃)—◁ | 184–185 |
| 3.014 | H | H | CH[CH(CH₃)₂]₂ | 195–197 |
| 3.015 | H | 4-Chlor-phenyl | C(CH₃)₃ | 320–322 |
| 3.016 | H | H | C(CH₃)₂CH=CH₂ | 227–229 |
| 3.017 | H | H | cyclopentyl | 240–242 |
| 3.018 | H | H | CH(CH₂CH₃)₂ | 182–184 |
| 3.019 | H | H | cyclohexyl | 249–251 |
| 3.020 | H | H | CH(CH₃)CH₂CH₂—C₆H₅ | 176–181 |
| 3.021 | H | H | CH₂CH(CH₃)CH₂—⌬—C(CH₃)₃ | 190–193 |
| 3.022 | H | H | C(CH₃)₂CH(CH₃)—C₆H₅ | 170–178 |

TABLE 4

| No. | R | mp [°C.] |
|---|---|---|
| 4.001 | C(CH₃)₃ | 299–300 |
| 4.002 | CH(CH₃)₂ | 301–304 |
| 4.003 | nonyl | 221–223 |
| 4.004 | cyclopropyl | 295–298 |
| 4.005 | CH(CH₃)CH₂OCH₃ | 266–269 |
| 4.006 | CH(CH₃)—◁ | 310–311 |
| 4.007 | CH(CH₃)C₆H₅ | 277–279 |
| 4.008 | C(CH₃)₂CH=CH₂ | 309–311 |
| 4.009 | CH(CH₂CH₃)₂ | 298–301 |
| 4.010 | cyclopentyl | 302–303 |
| 4.011 | cyclohexyl | 300–302 |
| 4.012 | CH(CH₃)CH₂CH₂C₆H₅ | 257–260 |

TABLE 4-continued

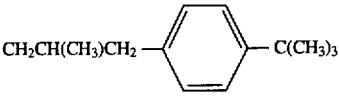

| No. | R | mp [°C.] |
|---|---|---|
| 4.013 | CH₂CH(CH₃)CH₂—⌬—C(CH₃)₃ | 234–237 |
| 4.014 | C(CH₃)₂CH(CH₃)C₆H₅ | 282–285 |

TABLE 5

| No. | R | mp [°C.] |
|---|---|---|
| 5.001 | C(CH₃)₃ | 298–300 |
| 5.002 | CH(CH₃)₂ | 278–280 |
| 5.003 | C(CH₃)₂CH=CH₂ | 266–270 |
| 5.004 | cyclopropyl | 311–313 |
| 5.005 | CH(CH₃)—cyclopropyl | 277–279 |

TABLE 6

| No. | R | M | mp [°C.] |
|---|---|---|---|
| 6.001 | C(CH₃)₃ | K | 256–257 |
| 6.002 | cyclopropyl | K | 292–294 |

TABLE 7

| No. | R | R' | mp [°C.] |
|---|---|---|---|
| 7.001 | CH(CH₃)₂ | CH₃ | 250–252 |

TABLE 8

| No. | R | mp [°C.] |
|---|---|---|
| 8.001 | CH(CH₃)₂ | 236–239 |

TABLE 9

| No. | R | mp [°C.] |
|---|---|---|
| 9.001 | CH(CH₃)₂ | 210–212 |
| 9.002 | C(CH₃)₃ | 220–222 |
| 9.003 | C(CH₃)₂CH=CH₂ | 207–209 |
| 9.004 | cyclopropyl | 250 |
| 9.005 | CH(CH₃)—cyclopropyl | 185–190 |
| 9.006 | (S) CH(CH₃)C₆H₅ | 234–236 |

TABLE 10

| No. | R | mp [°C.] |
|---|---|---|
| 10.001 | CH(CH₃)₂ | 254–258 |
| 10.002 | CH(CH₃)—cyclopropyl | 218–221 |
| 10.003 | cyclopropyl | 291 |

TABLE 11

| No. | R | mp [°C.] |
|---|---|---|
| 11.001 | CH₂CH(CH₃)CH₂—C₆H₄—C(CH₃)₃ | 240–244 |
| 11.002 | CH(CH₃)₂ | 270–276 |
| 11.003 | cyclopropyl | 292–295 |
| 11.004 | C(CH₃)₃ | 260–262 |
| 11.005 | CH(CH₃)CH₂OCH₃ | 245–246 |
| 11.006 | CH(CH₃)—cyclopropyl | 244–245 |

Use examples

The herbicidal action of compounds I is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for postemergence treatment was 3 kg/ha of active ingredient.

The pots were set up in the greenhouse at temperatures specific to their species, either at from 20° to 35° C., or from 10° to 25° C. The experiments were run for from 2 to 4 weeks. During this period the plants were tended and their reactions to the various treatments assessed.

The assessment scale was 0 to 100, 100 denoting non-emergence or complete destruction of at least the visible plant parts, and 0 denoting no damage or normal growth.

The following plants were used in the greenhouse experiments:

| Botanical name | Common name |
| --- | --- |
| Cerntaurea cyanus | cornflower |
| Setaria italica | foxtail millet |
| Bromus spp. | brome species |

The compounds of examples 3.002–3.004 and 3.009, 3.012 and 3.013, applied postemergence at a rate of 3 kg/ha, had a very good action on the unwanted plants mentioned above. The compound of example 1.001 combated *Centaurea cyanus* effectively.

Compounds nos. 3.007, 3.009 and 3.012 were applied at a rate of 1 kg/ha in rice, wheat, soybeans and cotton. A good herbicidal action was ascertained on *Digitaria sanguinalis, Abutilon theophrasti, Amaranthus retroflexus, Chenopodium album* and *Matricarla inodora*.

We claim:

1. Heteroaromatically condensed hydroxypyridonecarboxamides of the structure I

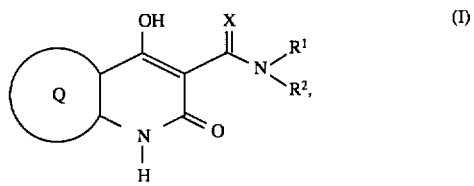

where the substituents and the ring have the following meanings:

$R^1$ hydrogen, hydroxyl, $C_1$–$C_{12}$-alkyl, $C_3$–$C_{12}$-alkenyl, $C_3$–$C_{12}$-alkynyl, $C_3$–$C_8$-cycloalkyl or $C_1$–$C_{12}$-alkoxy, wherein the alkyl, alkenyl, alkynyl, cycloalkyl or alkyl portion of the alkoxy group is substituted or unsubstituted;

$R^2$ hydrogen, $C_1$–$C_{12}$-alkyl, $C_3$–$C_{12}$-alkenyl, $C_3$–$C_{12}$-alkynyl, $C_3$–$C_8$-cycloalkyl, $C_3$–$C_8$-alkenyloxy or di-$C_1$–$C_4$-alkylamino wherein the alkyl, alkenyl, alkynyl, cycloalkyl, alkenyl portion of the alkenyloxy or the di-alkyl portion of the di-alkylamino group is substituted or unsubstituted;

or $R^1$, $R^2$ together denote a $C_2$–$C_6$-alkylene chain, wherein the alkylene chain is uninterrupted or is interrupted by oxygen, sulfur or N-methyl;

X is oxygen or sulfur;

Q is a 5-membered heterocyclic ring which is unsubstituted or mono- to tri-substituted, and environmentally tolerated salts thereof.

2. Heteroaromatically condensed hydroxypyridonecarboxamides of the structure I as defined in claim 1, where the substituents $R^1$ and $R^2$ have the following meanings:

$R^1$ hydrogen, hydroxyl, $C_1$–$C_{12}$-alkyl, $C_3$–$C_{12}$-alkenyl, $C_3$–$C_{12}$-alkynyl, $C_3$–$C_8$-cycloalkyl or $C_1$–$C_{12}$-alkoxy, wherein the alkyl, alkenyl, alkynyl, cycloalkyl or alkyl portion of the alkoxy group is unsubstituted or substituted with halogen, cyano, $C_3$–$C_8$-cycloalkyl, $C_1$–$C_4$-alkoxy, $C_1$–$C_4$-alkylthio, $C_1$–$C_4$-haloalkylthio, $C_1$–$C_4$-haloalkoxy, di-$C_1$–$C_4$-alkylamino, phenyl, phenoxy or phenylthio, where the phenyl radicals in turn may carry from one to three of the following groups: halogen, $C_1$–$C_4$-alkyl, cyano, nitro, $C_1$–$C_4$-alkoxy, $C_1$–$C_4$-haloalkyl or $C_1$–$C_4$-haloalkoxy;

$R^2$ hydrogen, $C_1$–$C_{12}$-alkyl, $C_3$–$C_{12}$-alkenyl, $C_3$–$C_{12}$-alkynyl, $C_3$–$C_8$-cycloalkyl, $C_3$–$C_8$-alkenyloxy or di-$C_1$–$C_4$-alkylamino, wherein the alkyl, alkenyl, alkynyl, cycloalkyl or alkyl portion of the alkoxy group or the di-alkyl portion or of the dialkylamino group is unsubstituted or substituted with halogen, cyano, $C_3$–$C_8$-cycloalkyl, $C_1$–$C_4$-alkoxy, $C_1$–$C_4$-alkylthio, $C_1$–$C_4$-haloalkoxy, $C_1$–$C_4$-haloalkylthio, phenyl, phenoxy or phenylthio, where the phenyl radicals in turn may carry from one to three of the following groups: halogen, $C_1$–$C_4$-alkyl, $C_1$–$C_4$-alkoxy, cyano or nitro;

or $R^1$, $R^2$ together denote a $C_1$–$C_6$-alkylene chain, wherein the alkylene chain is uninterrupted or is interrupted by oxygen, sulfur or N-methyl, and environmentally tolerated salts thereof.

3. Heteroaromatically condensed hydroxypyridonecarboxamides of the formula I as defined in claim 1, where $R^1$ is hydrogen and $R^2$ is branched or straight-chain $C_1$–$C_{12}$-alkyl, $C_3$–$C_{12}$-alkenyl, $C_3$–$C_{12}$-alkynyl, $C_1$–$C_{12}$-alkoxy or $C_3$–$C_6$-cycloalkyl, wherein the alkyl, alkenyl, alkynyl, the alkyl portion of the alkoxy group or the cycloalkyl group is unsubstituted or substituted by halogen, $C_1$–$C_4$-alkoxy, $C_3$–$C_8$-cycloalkyl, unsubstituted or halogen- or $C_1$–$C_4$-alkyl-substituted phenyl.

4. A herbicidal composition containing a herbicidally effective amount of a heteroaromatically condensed hydroxypyridonecarboxamide of the formula I as defined in claim 1 and inert additives.

5. A process for combating the growth of unwanted plants, wherein the unwanted plants and/or their habitat are treated with a herbicidally effective amount of a heteroaromatically condensed hydroxypyridonecarboxamide of the formula I as defined in claim 1, or an environmentally tolerated salt thereof.

* * * * *